United States Patent [19]

Sullivan

[11] Patent Number: 5,094,618

[45] Date of Patent: Mar. 10, 1992

[54] INTERMITTENT THREADED DENTAL POSTS

[75] Inventor: Jerry F. Sullivan, Ridgewood, N.J.

[73] Assignee: Coltene/Whaledent, Inc., New York, N.Y.

[21] Appl. No.: 692,310

[22] Filed: Apr. 26, 1991

[51] Int. Cl.⁵ .......................... A61C 8/00; A61C 13/00
[52] U.S. Cl. .................................. 433/173; 433/175; 623/16
[58] Field of Search ..................... 606/72, 73, 60, 65; 433/173, 174, 175, 176

[56] References Cited

U.S. PATENT DOCUMENTS 4,524,761 6/1985 de Zbikowski ..................... 606/73
4,773,858 9/1988 Marquez .............................. 433/173

FOREIGN PATENT DOCUMENTS 0190981 1/1986 European Pat. Off. ............ 623/22
WO85/04568 10/1985 PCT Int'l Appl. ................... 606/73

Primary Examiner—David Isabella
Assistant Examiner—Debra S. Brittingham
Attorney, Agent, or Firm—Helfgott & Karas

[57] ABSTRACT

A dental post for securely retaining a dental restoration on a prepared tooth stub. The dental post is formed of an elongated cylindrical rod having intermittent thread segments which actively engage the death of the tooth stub and passive land portions in between the thread segments.

20 Claims, 3 Drawing Sheets

INTERMITTENT THREADED DENTAL POSTS

BACKGROUND OF THE INVENTION

This invention relates to dental posts, and more particularly to a dental post with intermittent threads which provide both active thread segments and passive land surfaces between the segments, to improve post retention within a prepared tooth stub on which a dental restoration will be erected, while maintaining tooth stress as a minimum.

Additionally, this invention relates to the use of the threaded active segments to provide thread-like impressions in the dentin of the tooth in the areas of the passive land surfaces of the post, which results in improved retention when a dental cement is used. Furthermore, this invention provides the benefits of the increased holding power of active surfaces while minimizing stress on the tooth stub. In one embodiment the thread segments of this invention extend only for a portion of the axial length of a post, and the remainder of the post is a passive surface containing contours for cement retention.

In restoring dentition, one procedure is to build up a dental prosthetic structure on a tooth stub. The tooth stub is initially prepared by cutting it down to provide a suitable support on which the prosthetic structure will be built. A bore is formed into the tooth stub in which a dental post is inserted. In one type of dental post, referred to as an active post, there are threads provided on the post and the post is threaded into the bore in the tooth stub. Other posts are referred to as passive posts and they are secured in the bore by means of cement. The passive dental post typically includes a contoured surface for improving its retention in the bore formed in the tooth stub. Suitable dental cement is used for retaining the dental post in the bore. Even active posts use some cement. However, in active posts the retention is mainly from the threads cutting into the dentin. A portion of the dental post extends upwardly above the surface of the tooth stub so that as the dental prosthetic structure is formed or built up onto the tooth stub, it is retained in place on the tooth stub by means of the extending portion of the dental post.

Various active and passive posts have been suggested in the prior art in order to improve the retention of a dental post within a bore in a tooth stub. By way of example, there has been suggested in U.S. Pat. Nos. 702,111; 4,515,565 and 4,846,685, posts with screw threads which are screwed into the root cavity of a tooth. Threaded engagement of a post into the dentin of a tooth has been determined to stress and weaken the tooth thereby contributing to its possible fracture. On the other hand, using passive posts produce less stress in the tooth. However, the retention of passive posts is not as great as that of active posts. To improve retention, various types of contoured surfaces have been suggested for the passive post. By way of example, U.S. Pat. No. 4,479,783, issued Oct. 30, 1984 for "Helically Fluted Dental Post", assigned to the assignee of the present invention, suggests contouring the surface of a passive dental post with helical flutes in a sequence with designated flutes being deeper than alternating shallow flutes to improve retention of the dental post. Improvements in the capabilities of dental posts are also described in U.S. Pat. No. 4,729,736, issued Mar. 8, 1988 for "Contoured Dental Posts", assigned to the assignee of the present invention, including helical grooves and annular retaining ledges axially spaced along the post to both improve retention of the post and increase the strength of the post to reduce the possibility of post shear.

In a co-pending application, Ser. No. 303,900, filed Jan. 30, 1989, there is suggested the use of a dental post having an active threaded portion along an axial portion of the post and a passive portion axially along the rest of the post in order to receive the benefits of the increased holding power of a threaded active portion. In order to avoid stressing the tooth with the active portion, a sleeve with a threaded active portion is formed in a tooth stub. The threaded active portion of the post is then engaged with the threaded active portion of the sleeve to hold the post in the tooth stub. While the use of the threaded sleeve reduces stress, an additional step of forming the sleeve has been added to the dental restoration process.

As will be described, the present invention provides the benefits of active surfaces on a dental post while minimizing stress and increasing the bond between the tooth and the passive surfaces on the dental post.

While the aforementioned dental posts have provided improvements with respect to the retention of a post in a bore, still further improvements in such retention would be beneficial. These improvements would be particularly beneficial if they can be achieved without appreciably increasing the risk of breaking the dental post or the tooth.

SUMMARY OF THE INVENTION

Accordingly, it is an object of the present invention to provide an improved dental post.

A further object of the present invention is to provide a dental post having improved retention capabilities when secured in a prepared bore in a tooth stub.

Still a further object of the present invention is to provide a dental post having active surfaces and passive surfaces.

Still a further object of the present invention is to provide a dental post with threaded active surfaces and either smooth and/or contoured passive surfaces for securing the post to the tooth either with or without cement in the prepared bore.

Another object of the present invention is to provide a dental post with intermittent threads which provide a multiplicity of active thread segments and a multiplicity of passive intermittent land portions.

Still another object of the present invention is to use the intermittent threads to both hold the post in the dentin of a prepared tooth stub and to deform the dentin adjacent the intermittent land portions to increase the bond with the passive land portions by providing impressions in the dentin for a cement to fill and bond to.

Yet another object of the present invention is to provide a dental post having intermittent threads along a portion of its axial length and smooth or contoured surfaces along the remaining axial portions of its length.

Briefly, in accordance with the present invention there is provided a dental post for securely retaining a dental restoration on a prepared tooth stub. The dental post includes an elongated cylindrical rod with an elongated longitudinal axis. The rod has intermittent threads formed in the periphery of the rod with intermittent land portions between the intermittent threads.

The intermittent threads form active surfaces comprising individual segments which are threaded into the dentin of a tooth within a prepared bore in a tooth stub to retain the rod within the bore. As the intermittent threads engage the dentin, the dentin is cut into and is deformed. While the dentin has some elasticity, the depth of the threads is selected so that the dentin opposite the intermittent land areas remains deformed even after the intermittent thread has passed by. This will give the dentin the appearance of thread-like impressions even at the land areas.

In practice, a dental cement is introduced into the tooth stub bore prior to threading the post into the tooth stub. As the post is threaded into the tooth stub, the cement spreads about the rod moving into the land areas and into the thread-like impressions in the dentin opposite the land areas. In addition, some cement may spread over the intermittent threads of the post resulting in a thin layer of cement on the threads. The intermittent threads provide the benefits of increased retention of the active surfaces, and the intermittent land areas together with the cement which fills the impressions in the dentin provide improved passive surface retention. Furthermore, while each thread causes stress on the tooth stub, the land areas adjacent each thread provide stress relief thereby minimizing stress on the tooth stub.

In various embodiments of the invention, the shape, pitch and frequency of the thread segments are varied. In one of the embodiments, the intermittent threads extend only for a portion of the axial length of the rod and the remainder of the axial length of the rod has a smooth or contoured passive portion.

The aforementioned objects, features and advantages of the invention, will, in part, be pointed out with particularity, and will, in part, become obvious from the following more detailed description of the invention taken, in part, with the drawings which form an integral part thereof.

BRIEF DESCRIPTION OF THE DRAWINGS

In the drawings.

In the various figures of the drawings like reference characters designate like parts.

DETAILED DESCRIPTION OF THE PREFERRED EMBODIMENT

Figure 6:
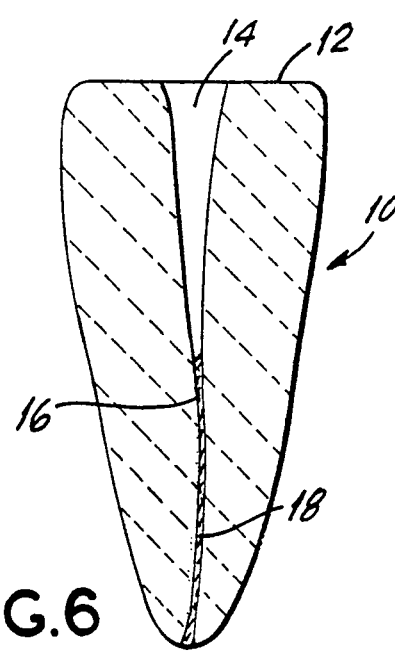
FIG. 6 is a cross sectional view taken through a tooth stub showing the initial preparation of the tooth stub for utilization of the dental post of the present invention.

Referring now to the drawings, in FIG. 6 there is shown a tooth stub 10 in cross section where the upper end of the tooth has been impaired. The tooth has been initially cut down, typically to provide a suitable upper surface 12 to support a dental restoration. In order to build up a dental restoration or other superstructure onto the tooth stub 10, there is required a retaining member, such as the dental post of the present invention.

Figure 7:
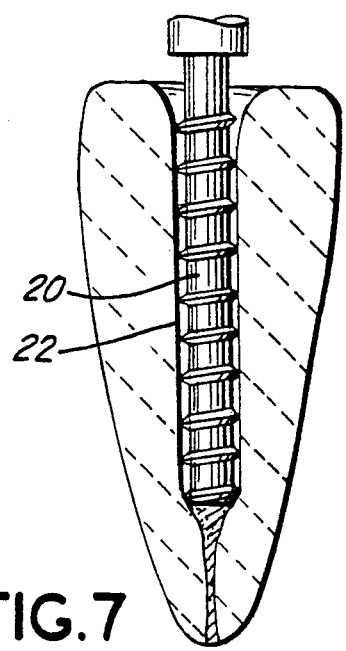
FIG. 7 is another view of the tooth stub shown in FIG. 6, being drilled to further open the canal in the tooth stub.

Initially, conventional root canal work is carried out by drilling and cleaning out the cavity 14 and the pulp along the canal section 16 of a tooth stub. The canal is sealed with a suitable sealant 18 such as gutta percha. As shown in FIG. 7 a twist drill 20 is used to drill an enlarged bore 22 into the canal section 16 of the tooth stub.

Figure 1:
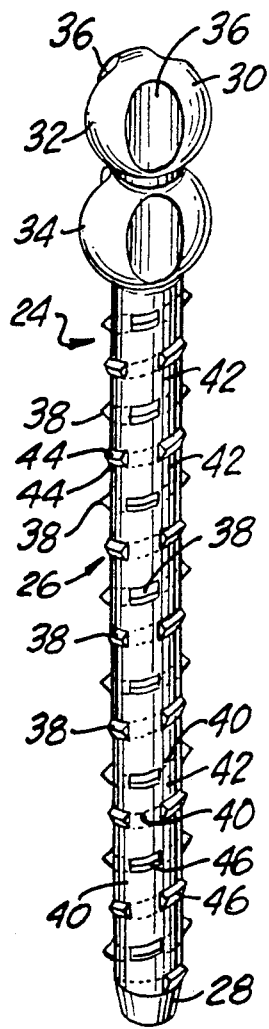
FIG. 1 is a perspective view of a dental post having intermittent threads and intermittent land portions in accordance with the principles of the present invention.

Referring to FIG. 1, the dental post of the present invention is shown generally as 24 and comprises an elongated cylindrical rod 26 having an elongated longitudinal axis and a substantially flat lower end 28 and a head 30 at its upper end. The head 30 includes a pair of spheres 32, 34 with elongated indentations 36 triangularly positioned about the spheres.

The rod 26 is intermittently threaded with thread segments 38 which are individual segments of what would otherwise be a continuous spiral thread of a given pitch. In between the thread segments 38, moving along the spiral thread path, are land portions 40 which are schematically depicted by dashed lines connecting the segments 38 for ease of description. It should be appreciated that these land portions are just part of the base post itself. Since, as will be described later, the thread segments 38 positively engage, cut into and deform the dentin of the tooth stub, the thread segments are also referred to as an active portion of the post 24. The land portions 40 and other unthreaded areas such as the space 42 which travels spirally about the rod 26 between the spiral turns of the threads are also referred to as passive portions of the post 24.

Figure 2:
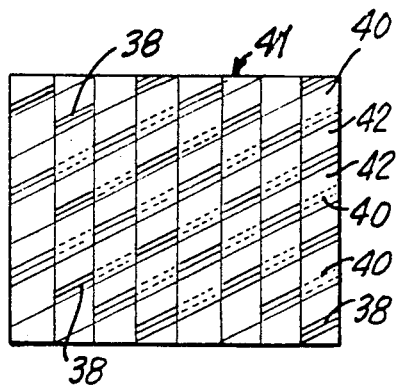
FIG. 2 is a view of the intermittent threads of the post in FIG. 1 shown schematically as unfolded along a portion of the length of the post.
Figure 4:
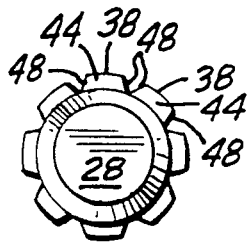
FIG. 4 is an end view of the dental post shown in FIG. 1 taken along line 4—4, showing the intermittent threads.

Referring to FIG. 2, there is a schematic view of the intermittent threads of the post 24 shown in FIG. 1. The individual segments 38 are shown schematically on an unfolded portion 41 of the post 24. Between the active segments 38 are passive land portions or areas 40 (shown dotted) and spiral spaces 42. As shown in FIG. 4, viewing post 24 from the lower end, the segments 38 are aligned and appear to horizontally touch one another, although each segment is at a different level than the adjacent segment. In one complete spiral circumference of the post there are eight thread segments.

Each thread segment 38, as part of a continuous spiral thread, has the shape of a typical thread. Each segment has sloped side walls 44. The sloped side walls meet at the apex of each segment in a sharp line 46. In addition, each segment 38 has slightly sloped end walls 48 which facilitate the thread segments cutting into the dentin of a tooth.

Figure 3:
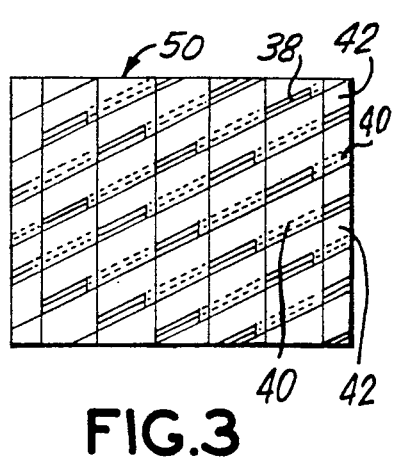
FIG. 3 is another unfolded schematic view of intermittent threads similar to the view shown in FIG. 2, in which the threads are spaced further apart.
Figure 5:
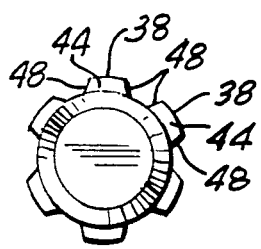
FIG. 5 is an end view similar to that shown in FIG. 4 in which the threads are spaced further apart as schematically shown in FIG. 3.

In FIG. 3, there is shown an unfolded portion 50 of a post similar to post 24 in which the thread segments 38 are spaced further apart from each other. In one complete spiral circumference of the post, there are six thread segments 38. The result of the spacing is to form larger land portions 40 (shown dotted). As shown in FIG. 5, viewing the post 24 from the lower end, the segments 38 are aligned, but do not appear to touch one another. The passive land portions 40 are larger in area than those shown in FIGS. 1, 2, and the spiral spaces 42 are the same in area. The result of combining the land portions 40 of FIG. 3 and the spiral spaces 42 of FIG. 3 is a greater overall passive portion of the post than in FIG. 2. Of course, the active portion is decreased.

The ratio of active to passive portions of a dental post 24 will affect the amount of stress a tooth stub is subjected to. The configurations of intermittent teeth shown in FIGS. 2 and 3 are one way of varying the stress and retention power of a post. There are other factors which affect retention power and tooth stress such as the post diameter and thread size relative to the bore 22 in the tooth stub 10. As will be described, there are variations on the number, size and shape of the intermittent teeth which affect ease of insertion into a prepared bore in a tooth stub and stress. Also, there are designs which combine intermittent threads with axial passive post sections without any threads in the passive sections, as will be described.

Figure 8:
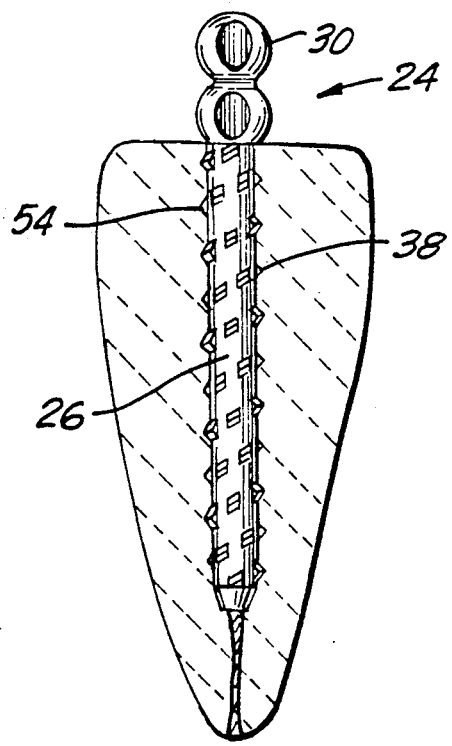
FIG. 8 is a cross sectional view of a drilled tooth stub with an open canal with the dental post shown in FIG. 1 threaded into the tooth stub.
Figure 9:
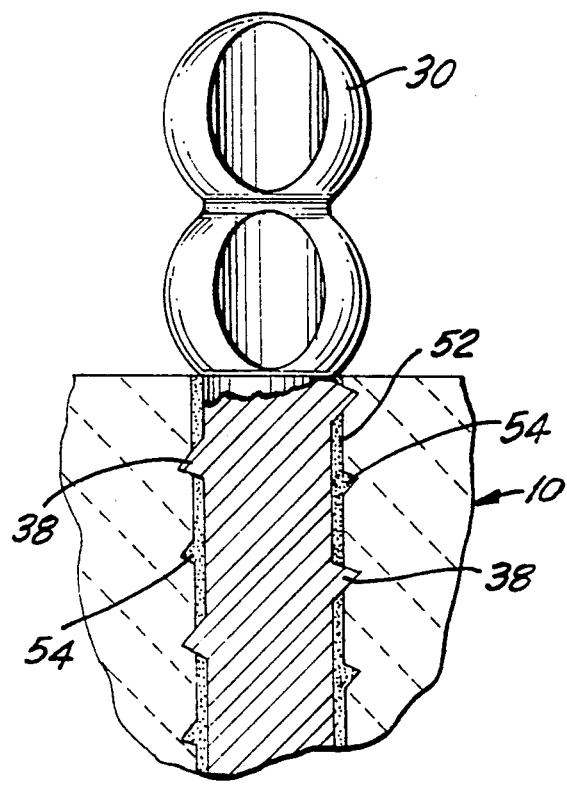
FIG. 9 is a fragmented, exploded cross sectional view of the tooth stub and post shown in FIG. 8 with a dental adhesive filling the land areas between the threads.

In use, dental post 24 is threaded into a prepared bore in a tooth stub 10 as shown in FIG. 8. The diameter of the rod 26 is selected to be slightly less than the diameter of the bore 22 and the outer sharp edge of each thread segment is sized to cut into and deform the dentin. Initially, a suitable dental cement 52 is placed in and about the bore 22 (FIG. 9). As the dental post 24 is threaded into the bore 22 the segments 38 cut into and deform the dentin. Recognizing that dentin is somewhat elastic, the thread segment diameter is selected relative to the bore diameter so that the deformed dentin retains a thread-like impression 54 after the threads passes.

As shown in FIG. 9, the dental cement spreads through the passive areas of the post 24 and also into the thread-like impressions 54 in the dentin. The passive areas act as vents as the post is threaded in for both air to escape and for the cement to spread into. A certain amount of cement may also spread onto the walls of each thread segment. Accordingly, the thread segments each form an active bond with the tooth and may be aided by a coating of cement on each segment. In addition, the passive positions of the post are held by the cement in the bore 22 and are aided by the cement in the thread-like impressions 54 in the dentin which form an interlock for retaining the post in the bore. The combination of active intermittent threads and passive areas causes less stress than a continuous thread of the same size. The retention power of the passive areas is protected against the cement shearing on the wall of the tooth by the cement filled impressions. In addition, shear along the passive post is prevented by the protruding thread segments.

Figure 10:
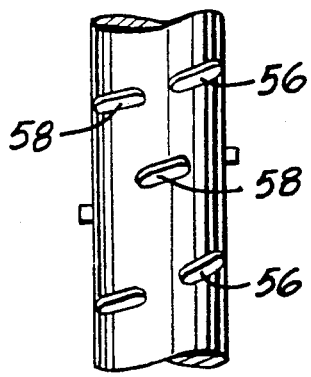
FIG. 10 is a perspective view of a portion of another embodiment of a dental post having enlarged oval threads with sharp outer edges.
Figure 11:
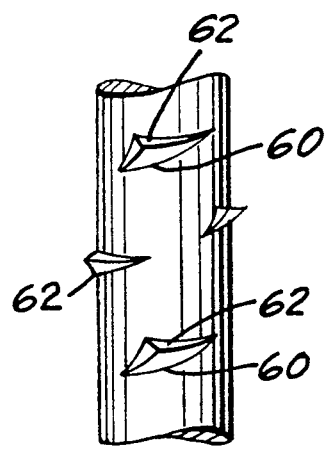
FIG. 11 is a perspective view of a portion of another embodiment of a dental post having elongated triangular threads with sharp outer edges.
Figure 12:
FIG. 12 is an end view of another embodiment of a dental post having trapezoidal shaped threads with sharp outer edges.

Referring to FIG. 10, an alternate embodiment of the thread segments is shown. In particular, each segment 56 is an elongated oval with a sharp outer edge 58. Another alternate embodiment of the thread segments is shown in FIG. 11. Each segment 60 is an elongated triangular thread with a sharp outer edge 62. Referring to FIG. 12, still another alternate embodiment of the thread segments is shown in which each segment 64 is trapezoidal in shape as viewed from the bottom.

The various thread shapes provide a variety of active surfaces which are useful in different dental applications. Certain shapes cut more easily into smaller diameter bores than other shapes, and certain shapes provide more holding power in short tooth stubs. In addition, the segment size will affect the depth of the thread-like impressions in the dentin in the land areas and thereby determine the retention in the passive areas of the post.

Figure 13:
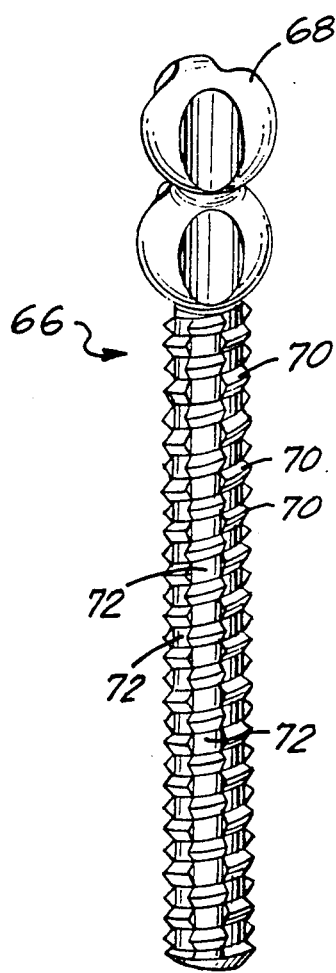
FIG. 13 is a perspective view of another embodiment of the dental post shown in FIG. 1 in which each spiral line of threads is adjacent another spiral line of threads.
Figure 14:
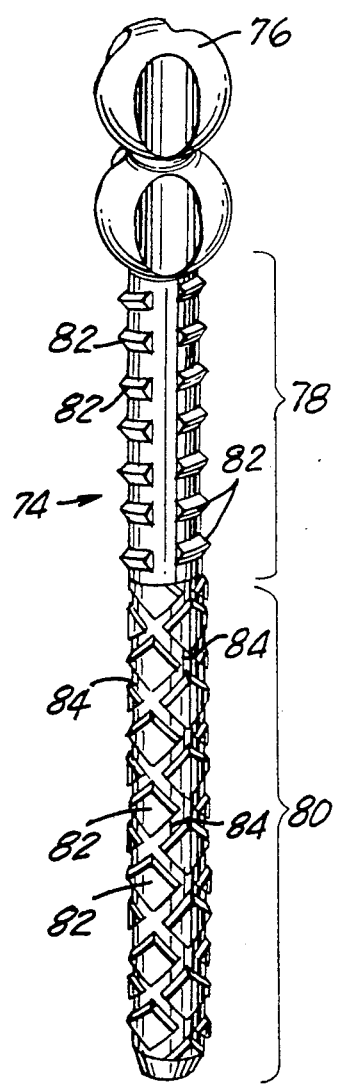
FIG. 14 is a perspective view of still another embodiment of the dental post shown in FIG. 1 in which the threaded active portion of the post extends for only a portion of the axial post length with the threads in vertical alignment, and the remainder of the axial length of the post is a contoured passive portion.
Figure 15:
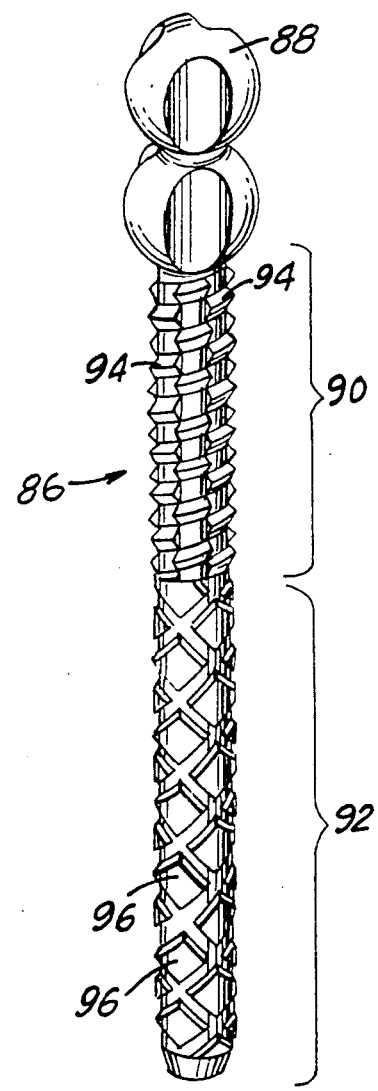
FIG. 15 is another embodiment of the post shown in FIG. 14 with the active portion having the thread arrangement shown in FIG. 13.

Further examples of post configurations are shown in FIGS. 13, 14, 15. Dental post 66 has a head 68 identical to the head shown in FIG. 1. The post 66 is threaded like an ordinary threaded screw with the thread spirals adjacent and touching one another, except that the threads are intermittent. In particular, there are thread segments 70 separated by land areas 72. Since adjacent thread spirals touch, there are no spiral spaces (such as spaces 42 in FIG. 1) between the thread spirals. This configuration provides a greater active area and a smaller passive area.

Referring to FIG. 14, a dental post 74 is shown with a head 76 identical to head 68. Post 74 has an axially positioned upper active portion 78 and a lower axially positioned passive portion 80. The active portion 78 has thread segments 82 identical in shape to those shown in FIG. 1, except that the segments are vertically aligned rather than staggered. The passive portion 80 is contoured to increase the retention of the post in a tooth bore. A series of raised diamonds are formed in the passive portion 80 as described in U.S. Pat. No. 4,729,736 issued to the assignee of this invention. A dental cement in a tooth bore will fill the grooves 84 between the raised diamonds providing a positive bond with the passive portion.

Referring to FIG. 15, a dental post 86 is shown similar to the post shown in FIG. 14. Post 86 has a head 88 identical to head 76 and also has an active portion 90 and a passive portion 92. Active portion 90 has intermittent thread segments 94 identical to those shown in FIG. 13 and passive portion 92 has raised diamonds 96 in a pattern identical to those shown in FIG. 14.

Numerous other configurations of the passive portions shown in FIGS. 14, 15 of the present invention are within the contemplation of the present invention. For example, the configuration described in aforementioned U.S. Pat. No. 4,729,736 which includes helical grooves and annular retaining ledges could be used.

It should be noted that the use of cement to increase the retention of the post 24 in a tooth stub, requires that the dimensions of the post and the bore be selected so that the cement will not interfere with placing the post in the tooth stub, i.e. there must be sufficient clearance between the post and the bore. Also, most likely, some cement will coat the thread segment and increase the retention of the active portion of the post. With the post 24 secured in the tooth stub 10, head 30 of post 24 extends upwardly above the upper surface 12 of tooth stub 10. A superstructure (not shown) can then be suitably formed onto the tooth stub in accordance with standard well known techniques in the dental line. The superstructure is retained onto the mating spheres 32, 34 and is held securely in place.

There has been described a preferred and alternate embodiments of the invention. However, it should be understood that various changes and modifications may be made thereto without departing from the spirit and scope of the invention.

What is claimed is:

1. A dental post for securely retaining a dental restoration on a prepared tooth stub in which the tooth stub has an enlarged bore in the canal section of the tooth stub, comprising:
   an elongated cylindrical rod having intermittent threads along a thread spiral in which each turn includes a plurality of active thread segments alternating with passiave land portions,
   said active thread segments having sharp outer edges capable of cutting into and deforming the dentin of the tooth when the dental post is inserted in the tooth.

2. A dental post as in claim 1, wherein the turns of the thread spiral are spaced apart by spiral passive spaces.

3. A dental post as in claim 2, wherein the turns of the thread spiral are in contact with one another in the direction of elongation of the rod.

4. A dental post as in claim 1, wherein the thread segments are vertically aligned to form vertical passive spaces therebetween.

5. A dental post as in claim 1, wherein the thread segments are staggered.

6. A dental post for securely retaining a dental restoration on a prepared tooth stub in which the tooth stub has an enlarged bore in the canal section of the stub, comprising:
   an elongated cylindrical rod having an active threaded portion along part of an axial length of the rod and a passive portion along part of the axial length of the rod, said active threaded portion having intermittent threads each turn divided into active thread segments and passive land portions between the thread segments,
   said active thread segments having sharp outer edges capable of cutting into and deforming the dentin of the tooth when the dental post is inserted into the tooth.

7. A dental post as in claim 6, wherein the turns of the thread spiral are spaced apart by spiral passive spaces.

8. A dental post as in claim 7, wherein the turns of the thread spiral are in contact wtih one another in the direction of elongation of the rod.

9. A dental post as in claim 6, wherein the thread segments are vertically aligned to form vertical passive spaces therebetween.

10. A dental post as in claim 6, wherein the thread segments are staggered.

11. A dental post as in claim 6, wherein the passive portion of the post has contoured raised portions to improve retention in the bore.

12. A dental post for securely retaining a dental restoration on a prepared tooth stub in which the tooth stub has an enlarged bore in the canal section of the stub, comprising:
   an elongated cylindrical rod having an active threaded portion along part of an axial length of the rod and a passive portion along part of the axial length of the rod, said active threaded portion having intermittent threads each turn divided into active thread segments and passive land portions between the thread segments,
   wherein the passive portion of the post has contoured raised portions to improve retention in the bore.

13. A dental post for securely retaining a dental restoration on a prepared tooth stub in which the tooth stub has an enlarged bore of a predetermined diameter in the canal section of the tooth stub, comprising:
   an elongated cylindrical rod having intermittent threads formed along a thread spiral in which the threads in each turn are divided into active thread segments and passive land portions between the thread segments,
   said active thread segments having sharp outer edges capable of cutting into and deforming the dentin of the tooth when the dental post is inserted in the tooth.

14. A dental post for securely retaining a dental restoration on a prepared tooth stub in which the tooth stub has an enlarged bore in the canal section of the tooth stub, comprising:
   an elongated cylindrical rod having intermittent threads provided along a thread spiral in which the threads in each turn are divided into active thread segments and passive land portions between the thread segments,
   said active thread segments having sharp outer edges capable of cutting into and deforming a dental cement pre-applied in said bore of the tooth, when the dental post is inserted in the tooth.

15. A dental post for securely retaining a dental restoration on a prepared tooth stub in which the tooth stub has an enlarged bore in the canal section of the tooth stub, comprising:
   an elongated cylindrical rod having intermittent threads along a thread spiral in which each turn includes active thread segments alternating with passive land portions,
   said active thread segments having sharp outer edges sized to cut into and deform the dentin of the tooth when the dental post is inserted in the tooth.

16. A dental post as in claim 15, wherein the thread segments are vertically aligned to form vertical passive spaces therebetween.

17. A dental post as in claim 15, wherein the thread segments are staggered.

18. A dental post as in claim 15, wherein the turns of the thread spiral are spaced apart by spiral passive spaces.

19. A dental post as in claim 15, wherein the turns of the thread spiral are in contact with one another in the direction of said rod.

20. A dental post for securely retaining a dental restoration on a prepared tooth stub in which the tooth stub has an enlarged bore in the canal section of the tooth stub, comprising:
   an elongated cylindrical rod having intermittent threads along a thread spiral in which the threads are divided into active thread segments and passive land portions between the thread segments, wherein the turns of the thread spiral are in contact with one another in the direction of elongation of said rod.

* * * * *